United States Patent
Massengill et al.

(10) Patent No.: US 6,592,222 B2
(45) Date of Patent: Jul. 15, 2003

(54) FLICKER AND FREQUENCY DOUBLING IN VIRTUAL REALITY

(75) Inventors: R. Kemp Massengill, Leucadia, CA (US); Richard J. McClure, San Diego, CA (US); Dariusz Wroblewski, Dan Diego, CA (US)

(73) Assignees: Massengill Family Trust, Leucadia, CA (US); Orincon, Corp., San Diego, CA (US)

( * ) Notice: Subject to any disclaimer, the term of this patent is extended or adjusted under 35 U.S.C. 154(b) by 96 days.

(21) Appl. No.: 09/900,764

(22) Filed: Jul. 2, 2001

(65) Prior Publication Data

US 2002/0047987 A1 Apr. 25, 2002

Related U.S. Application Data

(63) Continuation-in-part of application No. 09/467,360, filed on Dec. 20, 1999, which is a continuation-in-part of application No. 09/179,112, filed on Oct. 26, 1998, now Pat. No. 6,027,217, which is a continuation-in-part of application No. 08/700,754, filed on Jul. 31, 1996, now Pat. No. 5,864,384, and a continuation-in-part of application No. 08/864,331, filed on May 28, 1997, now Pat. No. 5,898,474.

(60) Provisional application No. 60/215,724, filed on Jul. 3, 2000, provisional application No. 60/136,151, filed on May 27, 1999, provisional application No. 60/165,082, filed on Nov. 12, 1999, provisional application No. 60/067,521, filed on Dec. 4, 1997, and provisional application No. 60/089,817, filed on Jun. 19, 1998.

(51) Int. Cl.[7] .................................................. A61B 3/02
(52) U.S. Cl. ....................................... 351/237; 351/201
(58) Field of Search ................................ 351/201, 200, 351/222, 224, 223, 226, 237, 239, 243, 246; 345/7; 600/558

(56) References Cited

U.S. PATENT DOCUMENTS 5,123,726 A   6/1992   Webster (List continued on next page.)

FOREIGN PATENT DOCUMENTS

DE    195 40 802.0    11/1993
GB    2096791 A    10/1982

OTHER PUBLICATIONS

Adams, A.; Clinical Measures of Central Vision Function in Glaucoma and Ocular Hypertension; Arch. Ophthalmol,; Jun., 1987; pp. 782–787; vol. 105..

(List continued on next page.)

Primary Examiner—George Manuel
(74) Attorney, Agent, or Firm—Gerald W. Spinks

(57) ABSTRACT

A system for testing and quantifying visual field and other visual function information in a head-mounted virtual reality environment, utilizing a directed image formation device for scanning of a flickering image for display to the test subject. A method and an apparatus are also provided for utilizing a central neural network and a central data bank to perform automatic interpretation of the visual function test parameters obtained in a plurality of visual field testing systems, for a plurality of patients, with control and response signals being transmitted via the Internet. The data produced by the testing systems are automatically analyzed and compared with patterns on which the neural network was previously trained, and clinical diagnoses for pathological conditions are thereby suggested to the respective clinician for each patient.

18 Claims, 7 Drawing Sheets

U.S. PATENT DOCUMENTS

| | | | |
|---|---|---|---|
| 5,461,436 A | 10/1995 | Campbell | |
| 5,467,104 A | 11/1995 | Furness, III et al. | |
| 5,530,495 A | 6/1996 | Lamprecht | |
| 5,589,897 A | 12/1996 | Sinclair et al. | |
| 5,596,339 A | 1/1997 | Furness, III et al. | |
| 5,623,925 A | 4/1997 | Swenson et al. | |
| 5,659,327 A | 8/1997 | Furness, III et al. | |
| 5,701,132 A | 12/1997 | Kollin et al. | |
| 5,751,465 A | 5/1998 | Melville et al. | |
| 5,894,338 A | 4/1999 | Miehle et al. | |
| 5,894,339 A | 4/1999 | Hosoi | |
| 5,903,397 A | 5/1999 | Melville et al. | |
| 5,910,834 A | 6/1999 | McClure et al. | |
| 5,969,871 A | 10/1999 | Tidwell et al. | |
| 6,033,076 A | 3/2000 | Braeuning et al. | |
| 6,045,227 A | 4/2000 | Stewart et al. | |
| 6,129,436 A * | 10/2000 | Treskov et al. | 351/201 |
| 6,139,152 A | 10/2000 | Ghahramani | |
| 6,145,991 A | 11/2000 | McClure et al. | |
| 6,290,357 B1 | 9/2001 | Massengill et al. | |
| 6,422,701 B2 * | 7/2002 | Wei et al. | 351/243 |

OTHER PUBLICATIONS

Adams, A.; Spectral Sensitivity and Color Discrimination Changes in Glaucoma and Glaucoma–suspect Patients; Invest. Oththalmol. Vis. Sci.; Oct., 1982; pp. 516–524; vol. 23, No. 4.

Alward, W.; Frequency Doubling Technology Perimetry for the Detection of Glaucomatous Visual Field Loss; American Journal of Ophthalmology; Mar., 2000; pp. 376–378; vol. 129, No. 3.

Burnstein, N., et al.; Comparison of Frequency Doubling Perimetry With Humphrey Visual Field Analysis in Glaucoma Practice; American Journal of Ophthalmology; Mar. 2000; pp. 328–333; vol. 129, No. 3.

Cello, K., et al.; Frequency Doubling Technology Perimetry for Detection of Glaucomatous Visual Field Loss; American Journal of Ophthalmology; Mar., 2000; pp. 314–321; vol. 129, No. 3.

Humphrey Instruments; Advertisement for Humphrey FDT Visual Field Instrument—Features and Specifications; 2 pages.

Iester, M., et al.; Frequency Doubling Technique in Patients with Ocular Hypertension and Glaucoma; Ophthalmology; Feb., 2000; pp. 288–294; vol. 107, No. 2.

Lachenmayr, B., et al.; Light–sense, Flicker and Resolution Perimetry in Glaucoma: A Comparative Study; Graefe's Archive for Clinical and Experimental Ophthalmology; 1991; pp. 246–251; vol. 229.

Lachenmayr, B., et al.; Diffuse and Localized Glaucomatous Field Loss in Light–sense, Flicker and Resolution Perimetry; Graefe's Archive for Clinical and Experimental Ophthalmology; 1991; pp. 267–273; vol. 229.

Lietman, T., et al; Neural Networks for Visual Field Analysis: How Do They Compare with Other Algorithms?; Journal of Glaucoma; 1999; pp. 77–80; vol. 8.

Patel, S., et al.; Algorithm for Interpreting the Results of Frequency Doubling Perimetry; American Journal of Ophthalmology; Mar., 2000; pp. 323–327; vol. 129, No. 3.

Plummer, D., et al.; Correlation between Static Automated and Scanning Laser Entopic Perimetry in Normal Subjects and Glaucoma Patients; Ophthalmology; Sep., 2000; pp. 1693–1701; vol. 107, No. 9.

Plummer, D., et al.; Scanning Laser Entopic Perimetry for the Screening of Macular and Peripheral Retinal Disease; Arch. Ophthalmology; Sep., 2000; pp. 1205–1210; vol. 118.

Sample, P., et al.; Visual Function–Specific Perimetry for Indirect Comparison of Different Ganglion Cell Populations in Glaucoma; Investigative Ophthalmology & Visual Science; Jun. 2000; pp. 1783–1790; vol. 41, No. 7.

Sekhar, G., et al.; Sensitivity of Swedish Interactive Threshold Algorithm Compared with Standard Full Threshold Algorithm in Humphrey Visual Field Testing; Ophthalmology; Jul., 2000; pp. 1303–1308; vol. 107, No. 7.

Sponsel, W., et al; Clinical Classification of Glaucomatous Visual Field Loss by Frequency Doubling Perimetry; American Journal of Ophthalmology, Jun., 1998; p. 830; vol. 125, No. 6.

Yamada, N., et al.; Screening for Glaucoma With Frequency–Doubling Technology and Damato Campimetry; Arch. Ophthalmology; Nov., 1999; pp. 1479–1484; vol. 117.

Zadnik, K.; The Ocular Examination Measurements and Findings; 1997; pp. 294–300; W.B. Saunders Company, Philadelphia, Pennsylvania.

Airaksinen, P.; Color Vision and Retinal Nerve Fiber Layer in Early Glaucoma; Feb., 1986; American Journal of Ophthalmalogy vol. 101; pp. 208–213.

Applegate, R.; Entoptic Evaluation of Diabetic Retinopathy; Apr., 1997; Investigative Ophthalmology & Visual Science, vol. 38, No. 5; pp. 783–791.

Applegate, R.; Entoptic Visualization of the Retinal Vasculature Near Fixation; Oct., 1990; Investigative Ophthalmology, vol. 31, No. 10; pp. 2088–2098.

Bartley, S.; Vision A Study of its Basis; 1963; pp. 57–71.

Bethke, W.; The Power of Second Sight; Jan., 1997; Review of Ophthalmology; p. 21.

Bottari, J.; Blue Field Entoptic Study: Diurnal and Long Term Fluctuation of Leukocyte Characteristics; www.c-s.tufts.ecu/~vanvo/ARVO96B.html; 1 p.

Breton, M.; Age Covariance Between 100–Hue Color Scores and Quantitative Perimetry in Primary Open Angle Glaucoma; May, 1987; Arch Ophthalmol, vol. 105; pp. 642–645.

Burstein, R.; Visual Retinal Display; 1997; HITLab Review, No. 10; 2 pages.

Business Communications Co.; Display Detects Retinal Diseases; Jun., 1999; Microtechnology NewsVvol. 5, No. 7; 2 pages.

Caprioli, J.; Early Diagnosis of functional Damage in Patients With Glaucoma; Jan., 1997; Arch Ophythalmol vol. 115; pp. 113–114.

CMP Media Inc.; Two Eye Virtual Retinal Display Tech-;Jun., 1997; EE Times Issue 957; 1 page.

Davies, E.; Macular Blood Flow Response to Acute Reduction of Plasma Glucoses in Diabetic Patients Measured by the Blue Light Entoptic Technique; Mar., 1989; Ophthalmalogy vol. 97 No. 2; pp. 160–164.

Donnelly, J., Here's Light in Your Eye, Kid; Mar., 1999; Military Training Technology, vol. 4, Issue 1; 3 pages.

Drance, S.; Acquired Color Vision Changes in Glaucoma; Jul. 1980/ Arch Ophthalmol vol. 99; pp. 829–831.

Falcao–Reis, F.M.; Mar., 1991; Macular Colour Contrast Sensitivity in Ocular Hypertension and Glaucoma; British Journal ofOphthalmology; 1991, 75; pp. 598–602.

Fellius, J.; Functional Characteristics of Blue–on–Yellow Perimetric Thresholds in Glaucoma; Feb. 8, 1995; Investigative Ophthalmology & Visual Science, vol. 36, No. 8; pp. 1665–1674.

Flammer, J.; Correlation Between Color Vision Scores and Quantitative Perimetry in Suspected Glaucoma; Jan., 1983;Arch Ophthalmol, vol. 102; pp. 38–39.

Geddes, J.; New Personal Display Technology; May 1999; Image Society Feature Articles; www.public.asu.edu/~image/NEWS/NewsFeatureA.html; 2 pages.

Gunduz, K.; Color Vision Defects in Ocular Hypertension and Glaucoma; Jan., 1988; Arch Ophthalmol vol. 106; pp. 929–935.

Hamill, T.; Correlation of Color Vision Deficits and Observable Changes in the Optic Disc in Population of Ocular Hypertensives; Jun., 1984; Arch Ophthalmol vol. 102; pp. 1637–1639.

Hart, W.; Color Contrast Perimetry; Nov., 1984; Ophthalmology vol. 92, No. 6; pp. 768–776.

Hart, W.; Color Perimetry of Glaucomatous Visual Field Defects; Oct., 1983; Ophthalmology vol. 91, No. 4; pp. 338–346.

Hart, W.; Color Contrast Perimetry; Jan. 1983; Investigative Ophthalmology & Visual Science vol. 25; pp. 400–413.

Hart, W.; Glaucomatous Visual Field Damage; Feb. 1989; Investigative Ophthalmology & Visual Science, vol. 31, No. 2; pp. 359–367.

Heron, G., Central Visual Fields For Short Wavelength Sensitive Pathways in Glaucomas and Ocular Hypertension; Jul. 1987; Investigative Ophthalmology & Visual Science vol. 29 No. 1; pp. 64–72.

Humphrey Instruments; Humphrey Blue–Yellow Perimetry; advertisement; date unknown; 1 page.

Humphrey Instruments; Humphrey Field Analyzer II; date unknown; www.humphrey.com; 1 page.

Interzeag AG; Blue/Yellow Perimetry; Jun., 1997; Ocular Surgery News; 1 page.

Interzeag AG; Clairvoyant Octopus; Jul. 1997; Ocular Surgery News; 2 pages.

Johnson, C.; Blue–on–Yellow Perimetry Can Predict the Development of Glaucomatous Visual Field Loss; Jan. 1993; Arch Ophthalmol vol. 111; pp. 645–650.

Johnson, C.; Progression of Early Glaucomatous Visual Field Loss as Detected by Blue–on–Yellow and Standard White–on–WhiteAutomated Perimetry;Jan. 1993; Arch Ophthalmol vol. 111; pp. 651–656.

Johnson, C.; Short–Wavelength Automated Perimetry in Low–,Medium–, and High–risk Ocular Hypertensive Eyes; Jan. 1995;Arch Ophthalmol vol. 113; pp. 70–76.

Kollin, J.; Optical Engineering Challenges of the Virtual Retinal Display; 1995; Published by Society of Photo–Optical Instrumentation Engineers; 12 pages.

Lewis, R.; Automated Perimetry and Short Wavelength Sensitivity in Patients with Asymmetric Intraocular Pressures; Nov. 1992; Graefe's Archive for Clinical and Experimental Ophthalmology; pp. 274–278.

Logan, N.; Detecting Early Glaucomatous Visual Field Changes With A blue Stimulus; Jan. 1983; American Journal of Ophthalmology vol. 95; pp. 432–434.

Massengill, R., GlobalMed VF–2400 Telemedicine/Autointerpretation System for Visual Function Testing; Nov. 1998; Press release for the American Academy of Ophthalmology Meeting; 7 pages.

Microvision, Web Site and Related Press Releases; Nov. 1999; www.mvis.com; Entire volume.

Microvison; Microvision Announces Breakthrough with Super–Bright Light–Emitting Diodes; Nov. 1999; www.mvis.com; 2 pages.

Microvision; Microvision and Boeing Collaborate to Develop Cockpit of the Future; Mar. 1999; www.mvis.com; 2 pages.

Microvision; Microvision Delivers Groundbreaking Helmet–Mounted Display; Mar. 1999; www.mvis.com; 2 pages.

Microvision; Virtual Retinal Display; May 1999; www.mvis.com; 9 pages.

Microvision; Microvision Chosen by Wallace–Kettering Neuroscience Institute; Aug. 1998; www.mvis.com; 4 pages.

Mindel, J.; Visual Field Testing With Red Targets; Jul. 1982; Arch Ophthalmol vol. 101; pp. 927–929.

Moss, L.; The Influence of Age–Related Cataract on Blue–onYellow Perimetry; Nov. 1994; Investigative Ophthalmology & Visual Science vol. 36, No. 5; pp. 764–773.

Moses, R.; Entoptic and Allied Phenomena; 1981; Adler's Physiology of the Eye; pp. 562–574.

Motolko, M.; The Early Psychophysical Disturbances in Chronic Open–angle Glaucoma; Nov. 1981; Arch Opthalmol vol. 100; pp. 1632–1634.

Ocular Surgery News; Beta Sites; Apr. 1999; 1 page.

Plummer, D.; The Utility of Entoptic Perimetry as a Screening Test for Cytomegalogvirus Retinitis; Feb. 1999; Arch Ophthalmol vol. 117; pp. 202–207.

Quigley, H., Chronic Glaucoma Selectively Damages Large Optic Nerve Fibers; Oct. 1986; Investigative Oophthalmology & Visual Science vol. 28 No. 6; pp. 913–920.

Sample, P.; Color Perimetry forAssessment of Primary Open–Angle Glaucoma; Sep. 1990; Investigative Ophthalmology & Visual Science vol. 31 No. 9; pp. 1869–1875.

Sample, P.; Isolating the Color Vision Loss in Primary Open–angle Glaucoma; Sep. 1988; American Journal of Ophthalmology vol. 106 No. 6; pp. 686–691.

Sample, P.; Progressive Color Visual Field Loss in Glaucoma; Dec. 1991; Investigative Ophthalmology & Visual Science vol. 33 No. 6; pp. 2068–2071.

Sample, R.; Short–wavelength Automated Perimetry Without Lens Density Testing; May 1994; American Journal of Ophthalmology vol. 118 No. 5; pp. 632–641.

Sample, P.; Short–wavelength Color Visual Fields in Glaucoma Suspects at Risk; Oct. 1992; American Journal of Ophthalmology vol. 115 No. 2; pp. 225–233.

Stoll, D.; Retinal Scanning Leads HMD Race; Dec. 1998; Photonics Online; 7 pages.

Wild, J.; The Statistical Interpretation of Blue–on–Yellow Visual Field Loss; Jul. 1994; Investigative Ophthalmology & Visual Science vol. 36 No. 7; pp. 1398–1410.

Yamazaki, Y.; A Comparison of the Blue Color Mechanism in High–and Low–tension Glaucoma; Jun. 1988; Ophthalmology vol. 96 No. 1; pp. 12–15.

Yamazaki, Y.; Correlation Between Color Vision and Highest Intraocular Pressure in Glaucoma Patients; Jul. 1988; American Journal of Ophthalmology vol. 106 No. 4; pp. 397–399.

Yu, T.; Peripheral Color Contrast; Apr. 1991; Investigative Ophthalmology & Visual Science vol. 32 No. 10; pp. 2779–2789.

* cited by examiner

FLICKER AND FREQUENCY DOUBLING IN VIRTUAL REALITY

CROSS REFERENCE TO RELATED APPLICATION

This is a continuation-in-part patent application of U.S. patent application Ser. No. 09/467,360, filed on Dec. 20, 1999, and entitled "Visual Function Testing with Virtual Retinal Display, " which is a continuation-in-part patent application of U.S. patent application Ser. No. 09/179,112, filed on Oct. 26, 1998, and entitled "Automated Visual Function Testing Via Telemedicine, " now U.S. Pat. No. 6,027,217; which is a continuation-in-part of prior pending application Ser No. 08/700,754, filed Jul. 31, 1996, entitled "Visual Field Testing Method and Apparatus Using Virtual Reality", now U.S. Pat. No. 5,864,384; and prior pending application Ser. No. 08/864,331, filed May 28, 1997, entitled "Visual Field Testing Method and Apparatus", now U.S. Pat No. 5,898,474. This application also claims priority from U.S. Provisional Patent application Serial No. 60/215,724, filed on Jul. 3, 2000, entitled "Flicker and Frequency Doubling in Virtual Reality." The parent application also claimed priority from U.S. provisional Patent Application Serial No. 60/136,151, filed on May 27, 1999, and U.S. Provisional Patent Application Serial No. 60/165,082, filed on Nov. 12, 1999, both entitled "Visual Field Testing with Virtual Retinal Display. " The grandparent application also claimed priority from Provisional U.S. Patent Application No. 60/067,521, filed Dec. 4, 1997, entitled "Automated Visual Function Testing in Virtual Reality", and Provisional U.S. Patent Application No. 60/089,817, filed Jun. 19, 1998, entitled "Telemedicine for Autointerpretation of Visual Field Testing."

STATEMENT REGARDING FEDERALLY SPONSORED RESEARCH OR DEVELOPMENT

Not Applicable

BACKGROUND OF THE INVENTION

1. Field of the Invention

This invention relates to optical testing of the eye's sensitivity to light, and in particular to visual field evaluation, using a Virtual Reality system.

2. Background Art

In the field of medicine where disorders of the eye are treated, it is necessary to measure the sensitivity to light in various regions of the light-sensitive retina. So doing measures function, as well as quantifying disorders of the eye and the retina, the optic nerve, the optic chiasm, the visual pathways to the brain, and the brain itself. Visual field testing is mandatory for glaucoma diagnosis and treatment. Apparatus to measure the field of vision is used by ophthalmologists and optometrists for these purposes and is relatively complex in its various functions, some of which complexity tends to make the human patient become tired or lose attention to the test.

One particular, currently known, visual field testing strategy employs image patterns created by a technology called "flicker perimetry." In this method, high temporal frequencies of flicker stimulate, on a preferential basis, retinal ganglion cells projecting onto the magnocellular layers of the lateral geniculate body of the brain. Such projections of ganglion cells are called M-cell fibers, and these fibers primarily consist of large-diameter cell axons. Comprising only 3–5 per cent of all retinal ganglion cells, it is these large-diameter M-cell axons which are particularly susceptible to glaucomatous damage. As these M-cells are stimulated preferentially by flicker perimetry, this test has promise for determining early stages of glaucoma in patients who are glaucoma suspects.

Employing flicker perimetric visual testing strategies, localized flicker field deficiencies have been reported in patients who have conventional light-sense visual fields interpreted as normal. Flicker perimetry, then, by diagnosing damage to M-cells fibers before more generalized cellular damage occurs, may well have clinical value in differentiating ocular hypertension from primary-open angle glaucoma.

Additionally, it has been noted that flicker perimetry has the distinct advantage of being more resistant to blur, scattering, and image degradation than conventional light-sense automated perimetry. For patients with significant cataracts, the test light target in light-sense perimetry is often poorly visualized, resulting in visual fields of dubious quality. Since media opacification (typically cataracts) does not unduly influence flicker perimetry, the use of flicker perimetry can be quite useful for such patients. For older persons, then, this relative resistance to image degradation is an especially important advantage of flicker perimetry, as cataracts and subsequent visual degradation are far more prevalent in older persons.

An additional advantage of flicker perimetry related to its blur resistance of up to six diopters is that refractive lenses or glasses for distance or for near are generally not required to compensate for the patient's refractive error or for accommodation.

It is known to employ a method for flicker perimetry which determines the highest frequency of flicker (called the critical flicker frequency) which can be detected for a 100 percent contrast flicker target. Another known flicker perimetric strategy determines the minimum contrast required to detect flicker for a fixed temporal frequency or group of frequencies. This strategy uses primarily temporal frequencies of 2, 8, and 16 Hz.

At an even higher frequency, sinusoidal gradings at 25 Hz are employed in the table model Humphrey/Welch Allen "Humphrey FDT™ Visual Field Instrument." A phenomenon called "frequency doubling" is called into play with this instrument. Frequency doubling technology perimetry creates an illusion in which a low-spatial frequency sinusoidal grading, (less than 1 cycle per degree) undergoes high-temporal-frequency counterphase flicker (greater than 15 Hz). The stimulus then appears perceptually to have twice as many light and dark bars as are actually physically present. This illusion is mediated neurologically by the M-cells, described above, which project onto the magnocellular layers of the lateral geniculate body. Cello et al. noted in the *American Journal of Ophthalmology* that frequency-doubling perimetry "demonstrates high sensitivity and specificity for detection of early, moderate, and advanced glaucomatous field loss." Cello adds that frequency-doubling perimetry "provides a useful complement to conventional automated perimetry test procedures and can serve as an effective initial visual field evaluation for detection of glaucomatous visual field loss."

A new visual field testing strategy, called the Swedish interactive test algorithm (SITA™), has been introduced by Humphrey Systems for its light-sense automated perimetric system. This testing strategy is said to reduce the threshold time for visual field performance on the Humphrey visual field tester by approximately 50 percent, while preserving the same reliability. Cello et al. postulate that "similar methods could be applied to the threshold strategies for frequency-doubling technology perimetry," adding that "it is conceivable that a frequency-doubling technology perimetry threshold could be employed to reduce the testing time to approximately 2.0 to 2.5 minutes per eye, with test-retest reliability equivalent to that of current threshold methods." With this in mind, the present invention envisions the incorporation of new algorithms, such as described above, to reduce test time and enhance patient friendliness.

Two of the present inventors disclosed in U.S. Pat. No. 5,898,474, issued Apr. 27, 1999, a method and apparatus for using virtual reality principles for testing and quantifying visual information from the eye, the visual pathways, and the brain. A headgear configuration allows the patient to observe a field of view into which sequenced test stimulae are presented by an excitation device commanded by a computer. Interactive sensory feedback both to and from the patient enables computer-driven presentation and modulation of test stimuli to measure with precision such parameters as visual field performance, visual acuity, and color vision. Using this system allows the patient unprecedented freedom of movement of the head and body, thus minimizing or even eliminating the stress and fatigue common with conventional non-virtual-reality visual field testing systems.

BRIEF SUMMARY OF THE INVENTION

The purpose of the presently described method and apparatus for visual field testing is to allow the sensitivity of the visual field to be measured without the attendant stress of the patient, and yet to preserve accuracy. The means by which this is accomplished uses concepts and apparatus from Virtual Reality. Virtual Reality is a term applied loosely to the experience of an individual when exposed to the appearance of surroundings which are presented by interactive apparatus for stimulation of the senses. The primary cues are usually visual, supplemented by audio, and the feedback to the apparatus is generally by physical movements of the individual experiencing the Virtual Reality, such as pressing a button or a switch, or speaking into a microphone.

In the parent patent applications and the presently disclosed invention, a Virtual Reality visual field measuring method and a related apparatus use a head-mounted goggle or face mask unit to present visual and audio stimuli to a patient. The visual portion has both relatively fixed image information, and superimposed visual areas, which may vary in time, place, color, and intensity. These stimuli are generated and controlled by software in an associated computer, which receives interactive feedback stimuli from the patient. Such stimuli include, but are not limited to, direction of gaze sensing, eyelid movement and blinking, audio, and hand pressure signals on cue.

Content of the software is dictated by the need to provide technically acceptable protocols. Such protocols provide for examining wide and narrow fields of view, selected areas, such as the blind spot of the fovea, and measurements of thresholds for sensitivity to light intensity, or, if desired, color. These are usually done for one eye at a time, each looking at the same, or similar, field of views.

Active feedback sensing alerts the system to patient loss of attention in general, or loss of fixation in particular, for notation and reiteration of test stimuli. In the presently described method and apparatus, provision is also made for reiteration of individual test points when a result is found to be inconsistent with a predetermined norm, or when lack of concentration or poor cooperation becomes evident, with appropriate care taken to provide no leading cues which may cause false positive or false negative responses. The software allows optional restful imagery to be provided in the "background," in addition to a conventional, uniform featureless field. The imagery in various quadrants/areas may be patterns, or low-contract images, and may move quickly or slowly, and may have intensity, color, or temporal modulation. The intensity, color, location, and duration of the superimposed test points are displayed by conventional electronic means, such as are now used in image presentations. Such means include cathode-ray tube, electroluminescent, liquid crystal, and gas discharge panels. Alternatively, test information may be projected onto the retina by means of one, or more, virtual retinal display systems. A hard-copy printout documenting patient responses is provided for the physician's records.

The present invention employs flicker perimetry and a subset of flicker perimetry, frequency-doubling technology perimetry, in a head-mounted display visual field testing system. The head-mounted display element of the present invention can be in the form of goggles or other head-gear configuration, all of which allow unprecedented freedom of motion for the patient when compared to stationary visual-field testers, which preclude neck or head motion. Because refractive lenses or glasses for distance or for near are generally not required to compensate for the patient's refractive error or for accommodation, the head-mounted display of the present invention is less complex than one requiring compensation for the patient's refractive error and accommodation, and, consequently, is also more economical to manufacture. The present invention of utilizing flicker perimetry and frequency-doubling technology perimetry for visual field testing in a virtual reality head-mounted display setting is a novel advance in visual field/function testing. The excitation device providing the flicker signal and the frequency-doubling technology signal include projection systems whereby the signal is projected onto the display screen of the head-mounted display, or, alternatively, one or more virtual retinal display projection systems projecting the flicker signal and the frequency-doubling technology signal directly onto the patient's retina may be employed.

The flicker signal and the frequency-doubling technology signal can be varied in intensity, duration, color (such as, but not limited to, blue-on-yellow, or yellow-on-blue), frequency, size, and locus within the patient's visual field.

An object of the present system is to provide relief from the stress of being required to concentrate, without head movement, one's gaze at a fixed location. The gaze sensor may be multi-element, so as to allow the gaze to be detected in a small solid angular range and, within this range, the effective fixation will be deemed to be maintained. The software may include an interest-fixation icon which encourages the gaze to trace its motion within the allowed solid angle, thus avoiding fixation fatigue. The software keeps track of the location of the test point frame of reference within that solid angle of displacement, so as to provide accurate mapping of test data on the field of view presented to the retina.

In addition to visual field testing, it is certainly within the scope of this invention to employ flicker perimetry and frequency doubling technology perimetry to provide other Virtual Reality computer-driven, interactive testing capability, such as for visual acuity and color testing.

The novel features of this invention, as well as the invention itself, will be best understood from the attached drawings, taken along with the following description, in which similar reference characters refer to similar parts, and in which:

DETAILED DESCRIPTION OF THE INVENTION

A head-mounted visual display apparatus, which remains in a fixed spatial relationship to the patient's head during testing of the visual field, is adjustable to suit the individual patient, and is mounted on the patient's head by conventional means. A screen display is part of the head-gear and encompasses the maximum field of view required. Alternatively, one or more virtual retinal display (VRD) systems may be employed to project directly onto the patient's retina the sequenced flicker perimetry signals or the sequenced frequency-doubling technology perimetry test signals. The head-gear is provided with integral microphone and speaker, for audio communication and feedback, and a multi-element gaze-aim sensor array. This ensemble is connected, by appropriate means, to a computer which provides the necessary visual and audio stimuli for the patient, and which receives the feedback responses to enable interactive functioning of the system. A hand-operated switch is incorporated.

An element of the Virtual Reality testing system is that it allows the patient the freedom to shift his/her gaze, while in the test mode, without disruption of the process, thus relieving one of the causes of patient stress. Another feature provided is the ability to modulate the background scene brightness, contrast, color, optical stimulus size and detail, duration, and frequency of the test stimuli, all of which serve to relieve fatigue of the patient. Furthermore, the patient may move around bodily, since the head-gear is portable and, in addition, electrical interface to the computer may be wireless.

The occlusion of one eye while testing the fellow eye, required by conventional visual field testing, can be eliminated in the preferred embodiment, since both eyes can be tested simultaneously, or separately and independently, through the use of individual eye goggles, or an appropriate face mask, to provide gaze separation.

The description above is by no means exhaustive of possible configurations, as well as other preferred embodiments, within the scope of the invention as an interactive Virtual Reality visual testing system utilizing flicker perimetry and frequency-doubling technology perimetry.

Autointerpretation can be performed employing a neural-net based autointerpretation system, or, alternatively, a rule-based autointerpretation system. Telemedicine can be used, with the Internet as the preferred long-distance carrier, although other long-distance carriers can be optionally utilized.

Figure 1:
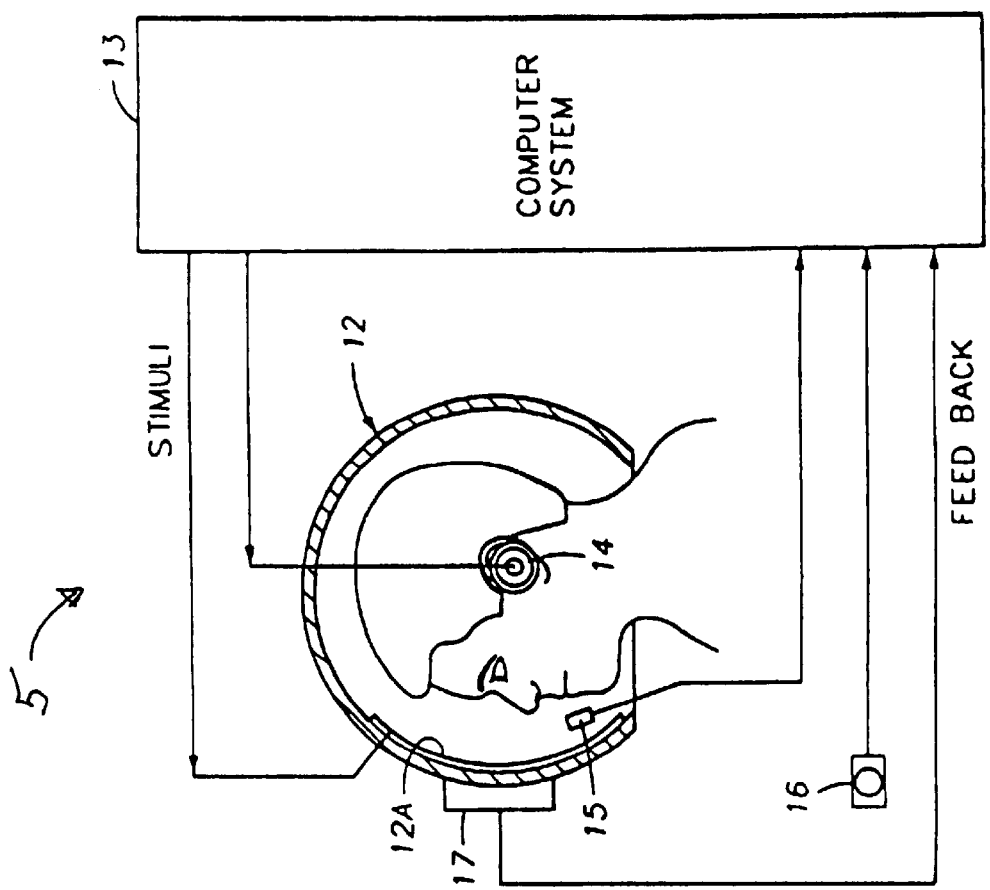
FIG. 1 is a schematic view of the apparatus of the present invention.

FIG. 1 shows a schematic of the virtual reality visual field testing system 5 of the present invention, in which a head-gear assembly 12 is connected to a computer 13, which delivers a visual signal to a head-gear display screen 12a, and an audio signal to a head-gear earphone 14.

The head-mounted visual display apparatus, head-gear 12, which remains in a fixed spatial relationship to the patient's head during testing of the visual field, is adjustable to suit the individual patient, and is mounted on the patient's head by conventional means. The screen display 12a is part of the head-gear 12 and encompasses the maximum field of view required. The head-gear 12 is provided with an integral microphone 15 and a speaker or earphone 14, for audio communication and feedback, and a multi-element gaze-aim sensor array 17. The microphone 15 provides feedback audio response to the computer 13. The head-gear assembly 12 is connected, by appropriate means, to the computer 13 which provides the necessary visual and audio stimuli for the patient, and which receives the feedback responses to enable interactive functioning of the system. A hand-operated switch 16 is incorporated to provide feedback to the computer 13, and the gaze sensor 17, mounted in the direction of gaze, provides optical gaze direction feedback to the computer 13.

Figure 2A:
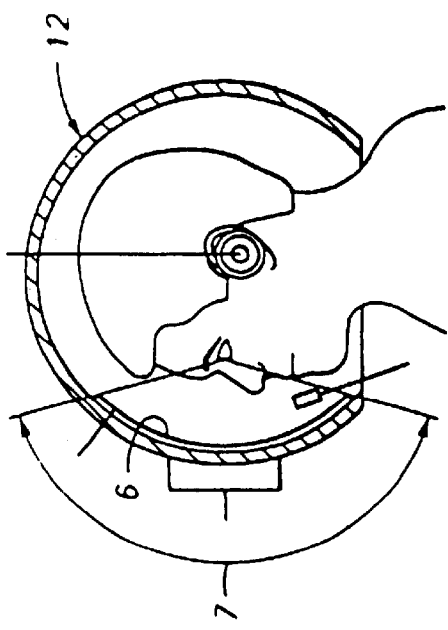
FIG. 2A is a schematic view of the apparatus of FIG. 1 measuring a vertical angular field of view.

FIG. 2A shows the vertical dimension 6 of an image surface covering a vertical angular field of view 7 on the screen display 12a.

Figure 2B:
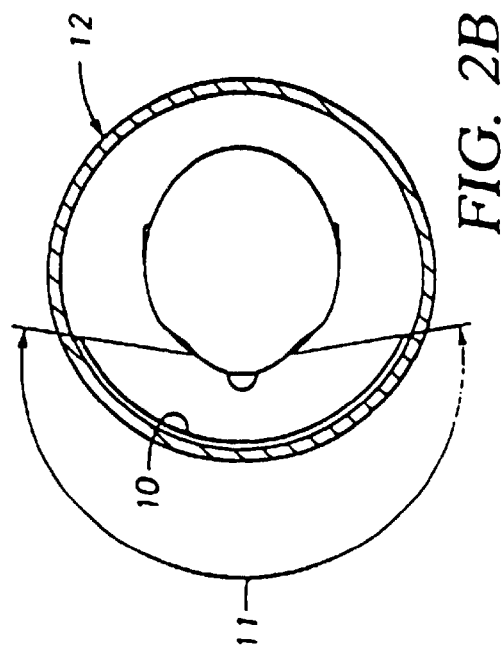
FIG. 2B is a schematic view of the apparatus of FIG. 1 measuring a horizontal angular field of view.

FIG. 2B shows the horizontal dimension 10 of an image surface covering a horizontal angular field of view 11 on the screen display 12a.

An element of the virtual reality visual field testing system is that it allows the patient the freedom to shift his/her gaze, while in the test mode, without disruption of the process, thus relieving one of the causes of patient stress. Another feature provided is the ability to modulate the background scene brightness, contrast, color, optical stimulus size and detail, and duration of the test stimuli, all of which serve to relieve fatigue of the patient. Of paramount significance is that the patient may move around bodily, since the head gear 12 is portable and, in addition, electrical interfaces to the computer 13 may be wireless.

Figure 3:
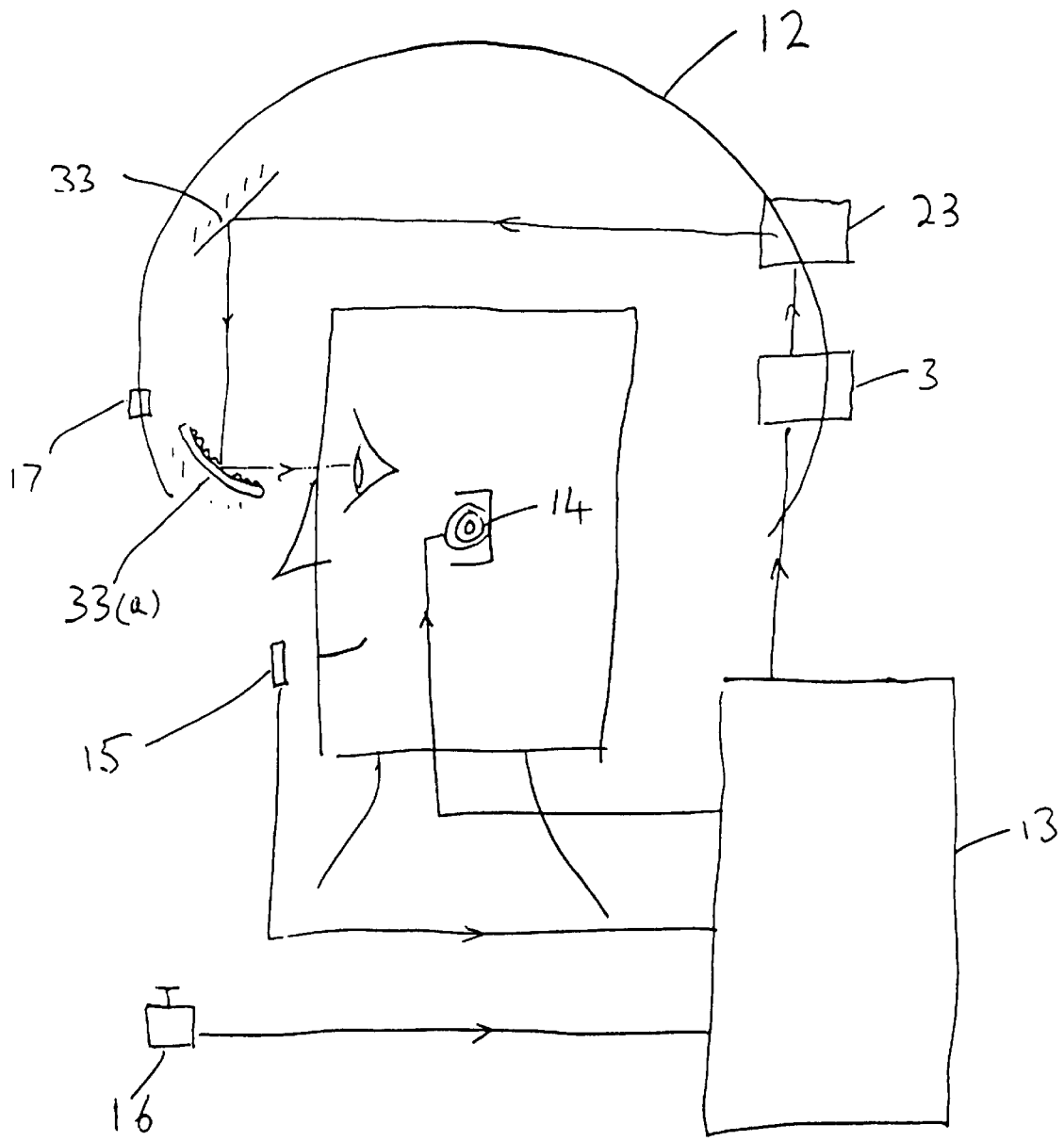
FIG. 3 is a schematic illustration of the present invention utilizing virtual retinal display technology.
Figure 5A:
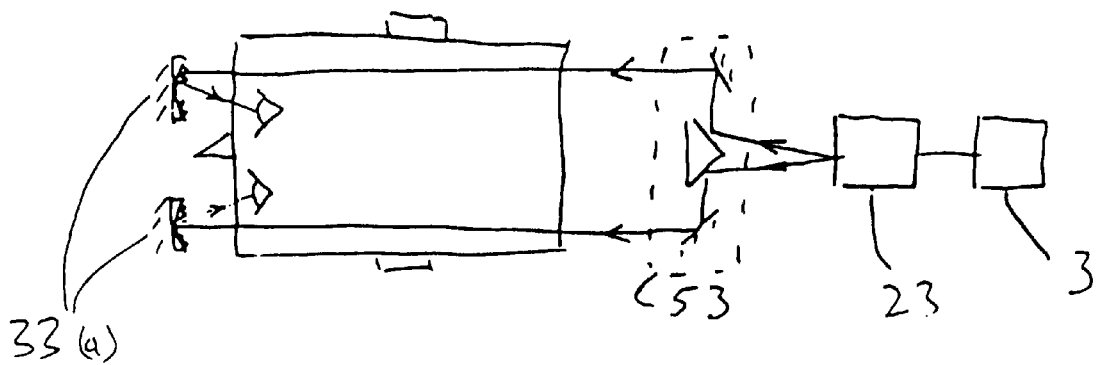
FIG. 5A is a schematic illustration of the apparatus shown in FIG. 3, with a beam splitter.

FIG. 3 shows the virtual-retinal-display preferred embodiment, in which a head-mounted apparatus 12, such as goggles, facemask, or other suitable head-gear, is connected to a computer 13. Software on the computer 13 is written to cause the computer 13 to generate a signal for the ultimate display of flicker perimetry, including frequency-doubling test strategies, through the papillary aperture onto the patient's retinae. These computerized image signals are transmitted to the virtual retinal display 3, which generates the visual images. The visual images are transmitted via a system of deflection and directing optics 23, a redirection mirror 33, and then to a curved Fresnel redirection mirror 33*a*, and thence into the eye through the pupil. Other redirection apparatus types and configurations can also be used, some of which are described below. The system of deflection and directing optics 23 provides angular deflection of the image beam in vertical and horizontal axes to direct the photon beam to the desired location upon the retina. A beam splitter 53, as depicted in FIG. 5A, can be used to split the image beam into two separate beams for projection onto the two retinae. The computer 13 also generates and transmits an audio signal to a head-mounted earphone 14. A microphone 15 provides a feedback audio response from the patient to the computer 13. A hand-actuated switch 16 provides manual feedback from the patient to the computer 13. An optical sensor 17, mounted in the direction of gaze, provides gaze direction feedback to the computer 13.

Figure 4A:
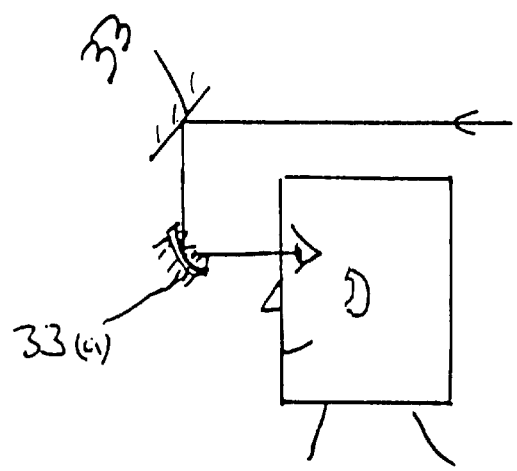
FIG. 4A is a schematic illustration of the apparatus shown in FIG. 3, with a curved Fresnel mirror redirection element.
Figure 4B:
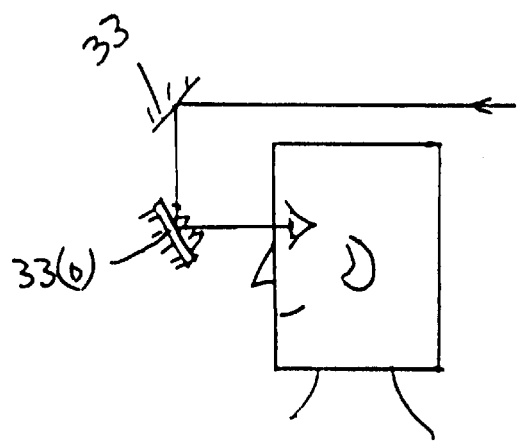
FIG. 4B is a schematic illustration of the apparatus shown in FIG. 3, with a flat Fresnel mirror redirection element.
Figure 4C:
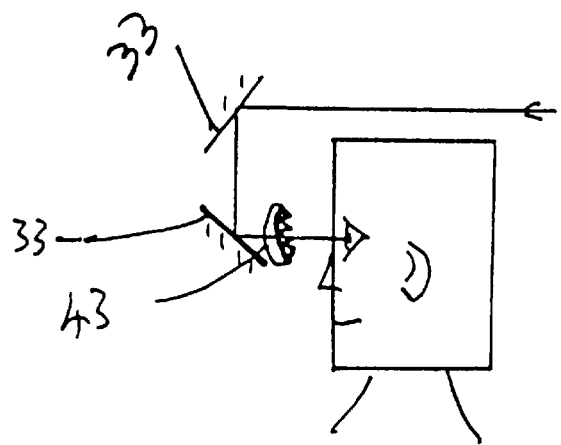
FIG. 4C is a schematic illustration of the apparatus shown in FIG. 3, with a dual mirror/Fresnel lens redirection element.

FIGS. 4A, 4B, and 4C depict alternate Fresnel optical element configurations for redirecting the image beam. The preferred embodiment is depicted in FIG. 4A, in which the final redirecting optical element is a curved Fresnel mirror 33*a*. An alternate embodiment is shown in FIG. 4B, in which a flat Fresnel mirror 33*b*, is incorporated. A further alternate embodiment is illustrated in FIG. 4C, shown dual redirecting mirrors 33, from which the stimulus passes through a curved Fresnel lens 43, en route to the eye. FIGS. 4A, 4B, and 4C, are intended to be merely a few examples of possible redirecting element configurations.

FIG. 5A depicts a schematic view of the virtual-retinal-display preferred embodiment, shown from the top to illustrate the projection of separate beams into the two eyes of the patient. This embodiment utilizes a single virtual retinal display 3, and a single system of deflection and direction optics 23, with the image passing through a beam splitter 53, which splits the beam into two image beams for further transmission to both eyes. Under the control of the computer 13, the image beam can be projected onto only one eye at a time, if desired. Thusly, both eyes receive computer-directed, sequenced stimuli from a single virtual retinal display 3, and from a single system of deflection and directing optics 23. This is more economical, lighter, and much more patient friendly.

Figure 5B:
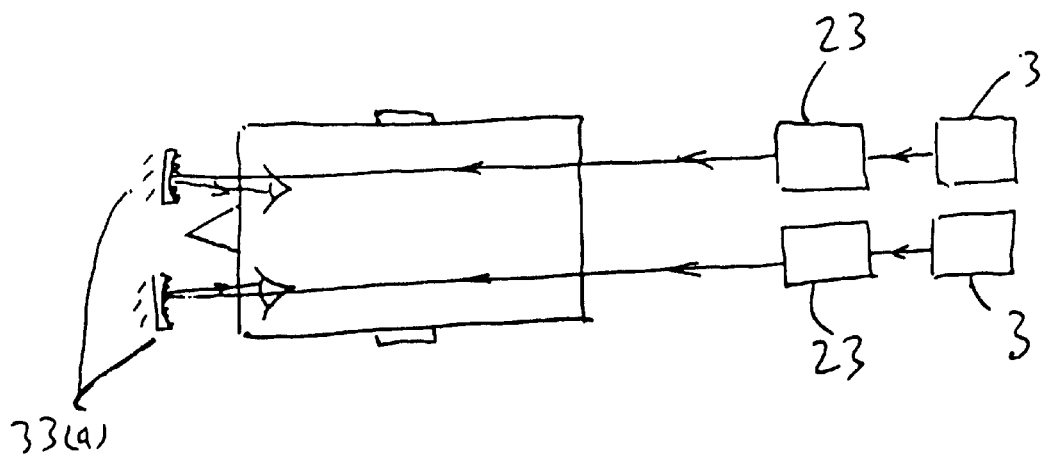
FIG. 5B is a schematic illustration of the apparatus shown in FIG. 3, with dual virtual retinal displays.

FIG. 5B shows an alternate embodiment incorporating dual virtual retinal displays 3, dual deflection and directing optics systems 23, and an absence of a beam splitter.

Figure 6A:
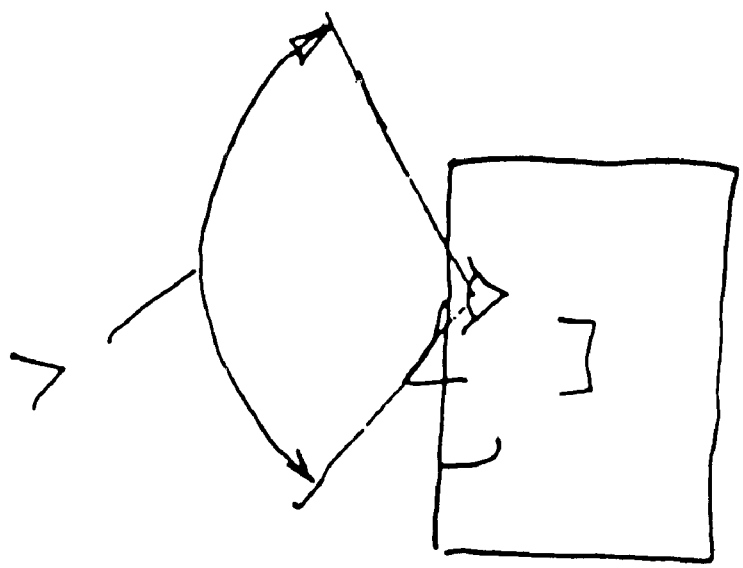
FIG. 6A is an illustration of the vertical field of view of the apparatus shown in FIG. 3.
Figure 6B:
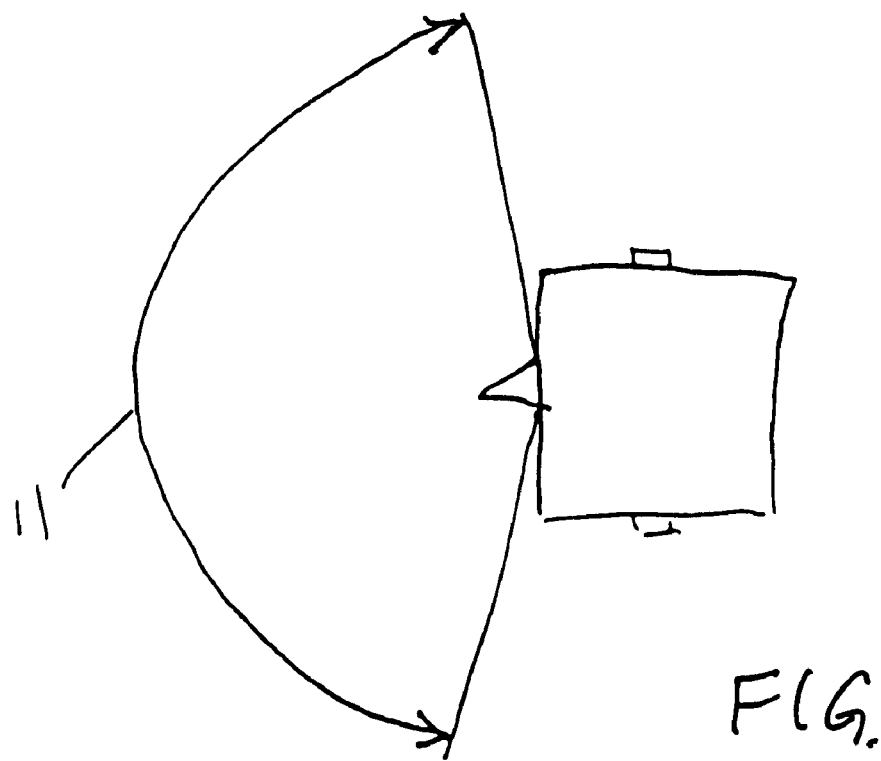
FIG. 6B is an illustration of the horizontal field of view of the apparatus shown in FIG. 3.

FIG. 6A illustrates a vertical angular field of view 7, over which flicker perimetry and frequency-doubling technology perimetry images can be displayed. FIG. 6B shows a horizontal angular field of view 11, over which flicker perimetry and frequency-doubling images can be displayed.

Figure 7:
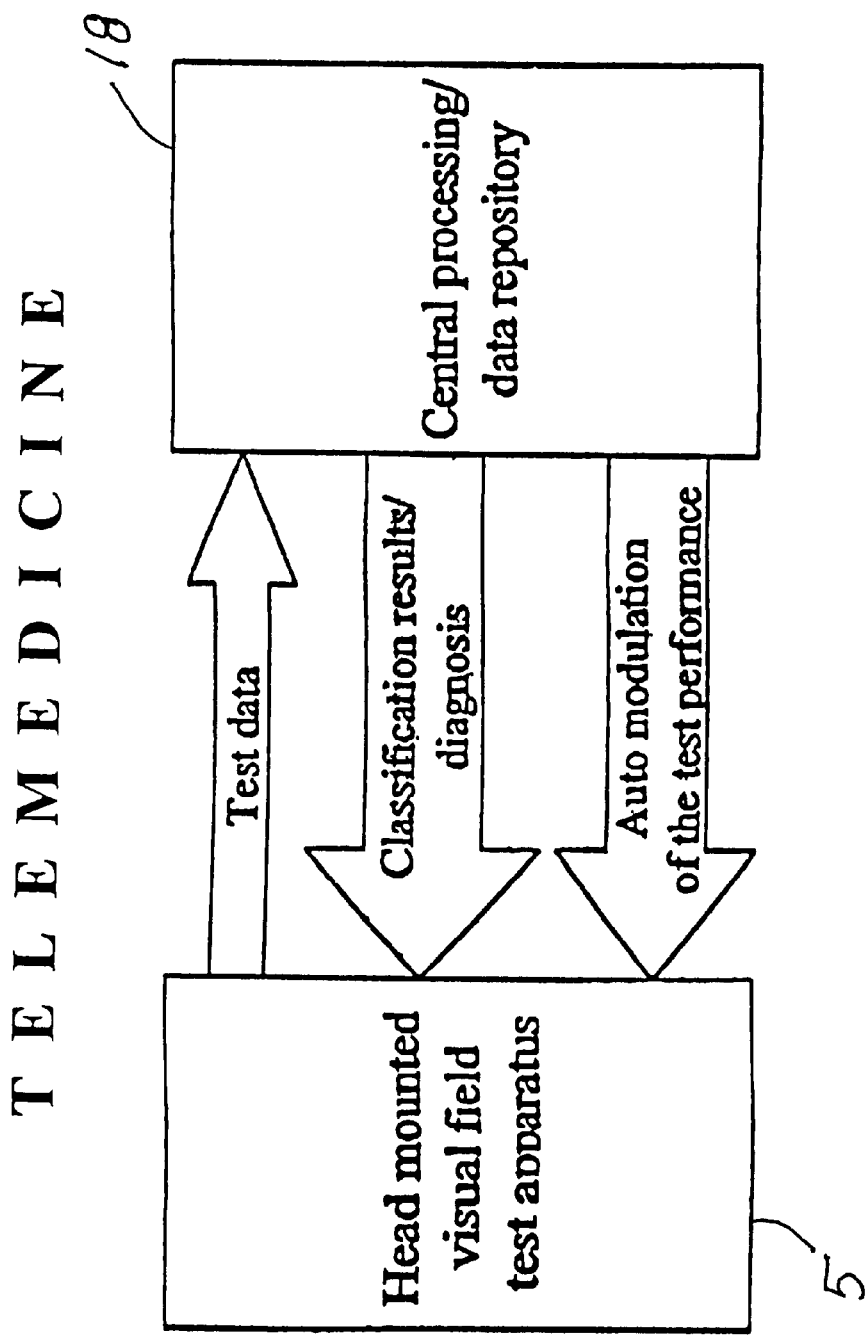
FIG. 7 is a schematic diagram of the information flow in the system of the present invention.

The system of the present invention, as illustrated in FIG. 7, includes a local visual field test apparatus 5, which can include a head-mounted virtual retinal display apparatus or other head-mounted display system 12, and a local processing system 13 which can form an integral part of the head-mounted diagnostic apparatus 12. The expert supervision of the testing process and interpretation of the results can be performed via long-distance transmission vehicles, such as the Internet, thus providing, telemetrically, not only essentially instantaneous autointerpretation, but also telemetric monitoring of the patient's performance of the test in real time. A central world-wide processing/data collection system 18 (consisting of a single station or a series of stations, such as one for the United States, one for Japan, one for France, etc.) can be linked via the Internet to a multitude of local test stations 5 and provide multiweb-like integration. The data processing portion of the system incorporates the local processing system 13 and the central processing system and data repository 18, to provide the classification of the visual field test data in terms of presence or absence of all diseases, or any particular disease (e.g., glaucoma). The data processing portion of the system also may assign a probability of detection and/or a numerical value indicating the severity of the disease. This provides a tool for monitoring disease progression.

Functions of the local processing system include the following:
(a) provision of flicker perimetry or frequency-doubling technology perimetry visual stimuli,
(b) automatic customization of the stimuli sequence based upon the patient response, including repetition of the stimuli for which no adequate response was registered (due either to the patient's loss of attention or to disease-induced damage to the visual field), and adjustment of the amplitude of stimuli, and
(c) pre-processing of the patient response data, such as elimination of those measurement points (patient's response) that are deemed inadequate, normalization to a pre-defined standard, and formatting for transmission to the remote processing system.

Functions of the remote processing system include the following:
(a) automatic interpretation of the visual field test data, and
(b) formulation of corrections to the data collection protocol, based upon the results of autointerpretation and comparative analysis employing the database of interpreted and medically verified visual field tests.

Figure 8:
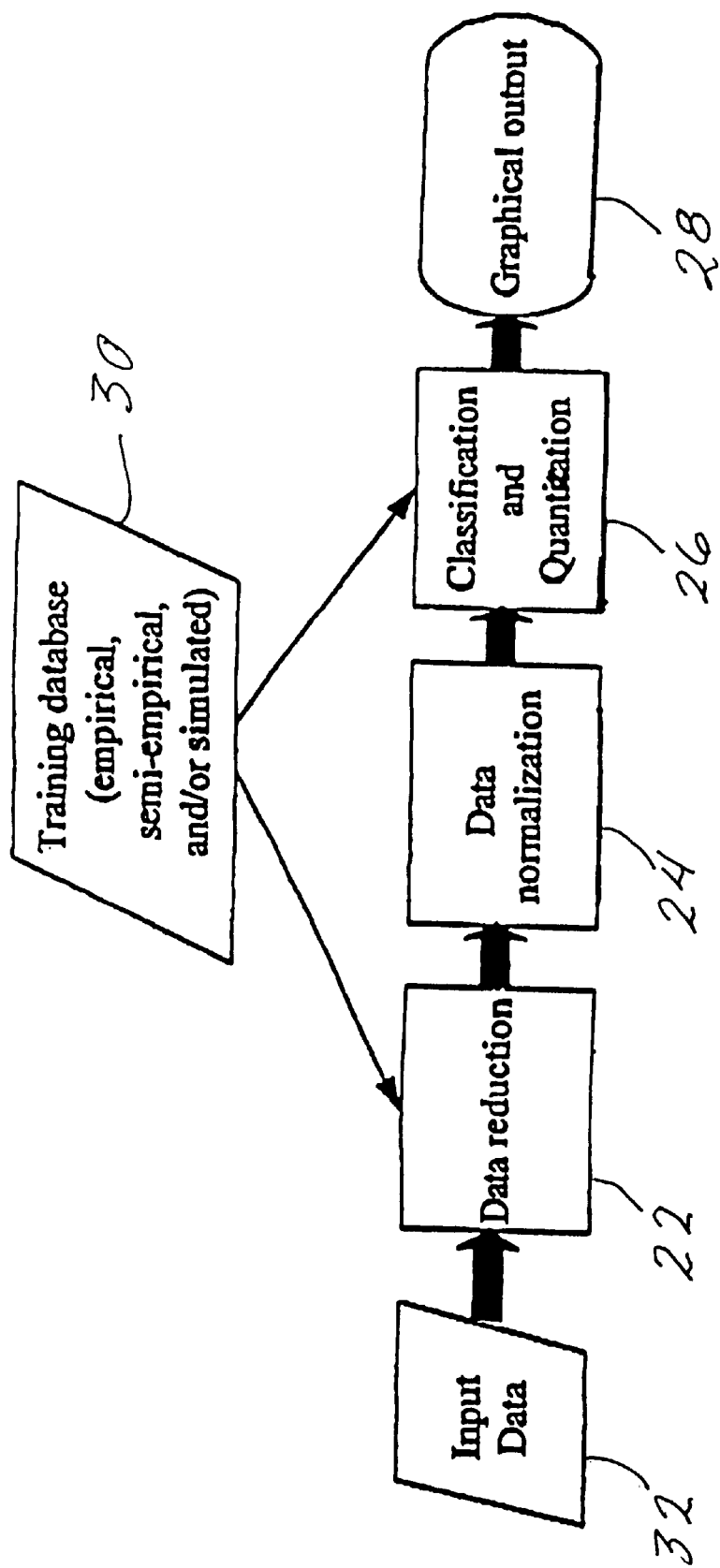
FIG. 8 is a schematic diagram of the automatic interpretation portion of the system of the present invention.

The central processing/data collection system 18 includes an automated interpretation system, incorporating a neural network, which functions as shown in FIG. 8. Integration of a multitude of local testing stations 5 into a world-wide system results in a telemedicine system which is "intelligent" in that ongoing data accumulation and analyses thereof improve the computational model and provide, over time, increasingly more accurate identification of very subtle disease processes.

A database of empirical, semi-empirical, or simulated visual field test data is used to build a neural network model of the visual field test data. This model, when applied to previously unseen test results, is capable of automatically interpreting and classifying the test data in terms of the presence and/or severity of abnormal (diseased) regions and states.

The autointerpretation system utilizes the results of visual stimuli (consisting of, with or without color, flicker perimetry or its subset, frequency-doubling technology perimetry) presented to the patient, which are converted into numerical representation for data processing. Other inputs, resulting from standard pre-processing of the test data, such as visual field indices, can also be employed by the neural network. Inclusion of all available individual components of flicker perimetry and frequency-doubling technology perimetry testing strategies is useful for proper clinical interpretation of the visual test examination. Thus, the information provided to the neural network may include:
(a) ancillary data, such as pupil size during testing, the patient's age, and visual acuity;
(b) reliability indices, such as fixation behavior and accuracy, and response fluctuation;
(c) visual field indices, such as average deviation of sensitivity at each test location from age-adjusted normal population values, the index of the degree or irregularity of visual field sensitivity about the normal slope, and sensitivity analysis of clusters of points;

(d) results of point-by-point comparison of test results with age-matched normal population values;

(e) results of flicker perimetry and of its subset, frequency-doubling technology perimetry; and, (f) other available tests.

The use of the entire gamut of available information for automatic interpretation by the neural network is also novel. Previously known neural network systems included only the straight visual field data.

The preferred embodiment of the neural network based autointerpretation system is shown in FIG. 8. The system consists of some or all of the modules described below. The data reduction module 22 is employed to reduce the size of the data vector presented to the neural network classifier 26. This module employs singular value decomposition, principal component analysis (PCA), learning vector quantization, or other clustering and data size reduction methods. Typically, application of any of the methods results in at least a two-fold decrease in the size of the data vector. Such a reduction increases the ability of the neural network to generalize the data contained in the training set. The clustering and linear decomposition methods (such as PCA) are also useful for "novelty detection," i.e., for establishing if the current data vector is outside the region encompassed by the training data set. The neural network model is likely to fail for such data and thus, the ability to detect novelty is crucial for minimizing the number of erroneous interpretations.

The data normalization module 24 performs amplitude normalization of the data presented to the neural network.

The neural network classifier module 26 performs pattern recognition and classification of the visual field test data. The probability of classification (or, degree of membership) is quantified for each of the classes considered in the model. In the preferred embodiment, a non-linear classification scheme exemplified by the multilayer perceptron or the radial/ellipsoidal basis function neural network used. However, other classification schemes, such as multivariate analysis, linear regression, statistical classifiers or discriminators (such as Bayesian classifiers) may also be employed. The neural networks are especially useful for the automatic application scheme because they provide a non-parametric, empirical model of the visual field test data and are computationally nonintensive, i.e., the classification computations can be performed quickly on inexpensive computers.

The neural network may be a binary classification system, which will indicate the presence or absence of a particular disease, such as glaucoma, or a multi-class system, which provides recognition and classification of a large variety of possible visual field disorders, including, but not limited to, neurological tumors, cerebrovascular accidents and strokes, optic nerve disorders, compression syndromes of the optic nerve or optic chiasm, demyelinating disease, and disease of the retina.

The implementation may be in the form of a single-level neural network system or a hierarchical system. In the single-level system, all the input data, which are deemed relevant for the interpretation task, are inputted and processed simultaneously. In the hierarchical system, different input data types are modeled by dedicated separate subsystems, and these outputs are subsequently fused through a suitable computational architecture, to produce the final classification result.

The output module 28 creates a graphical representation of the visual field test data, such as isopter/scotoma plots, or gray scale or color-coded plots, with superimposed identification of the regions that the system classified as abnormal.

The automatic interpretation system is an expert system trained on a set of empirical, semi-empirical, and/or simulated data 30. The construction of a proper training database is essential for achieving good performance of the interpretation system (good sensitivity and specificity). The training database may contain all, or any, of the following types of visual field data:

(a) empirical data, i.e., data obtained for patients with normal and abnormal visual fields as measured by flicker perimetry or frequency-doubling technology perimetry visual field testing;

(b) semi-empirical data, i.e., data obtained by modification of the empirical data, as described above, by:

(1) emphasizing or de-emphasizing certain aspects of the visual field test to bring out the characteristic features of certain diseased states;

(2) adding noise or measurement uncertainty components which may be associated with a real visual field examination; and, (3) any other modification of the visual field test data and their associated classification; and, (c) simulated data, i.e., data which are constructed to simulate the real-world results of a visual field test performed using flicker perimetry, including frequency-doubling testing strategies, for both normal and abnormal fields.

Training of the classification system is performed off-line with active participation of a human expert. That is, all visual field test data in the training database are examined by an expert, and the medical diagnosis is verified and validated before the data are used to build the neural network model. The centralized processing enables collection of a large number of diverse examples of normal and abnormal visual field test data. The novelty detection capability of the system alerts the system custodian to the necessity for expert examination of the novel data. After completion of such examination, the data may be included in the model by including the new data 32 in the training database and re-training the system.

Autointerpretation of the results obtained by flicker perimetry and its subset, frequency-doubling visual field testing, can also be performed utilizing a rule-based auto-interpretation system, as described in U.S. Pat. No. 6,145, 991, the disclosure of which is incorporated herein by reference. This system of autointerpretation, akin the neural net autointerpretation system described above, can also be appropriately utilized for telemedicine.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A visual function testing apparatus, comprising:

a light source, said light source being modulated to create a flickering image;

a scanning system, said scanning system being adapted to scan said flickering image from said light source for display to an eye of a patient;

a gaze sensing device adapted to sense the orientation of an eye of a patient and to generate a gaze orientation signal;

a response sensing device adapted to sense a patient's response to said flickering image and to generate a response signal; and a computer, said computer being connected to said light source to modulate said light source to create said flickering image, said computer being connected to said gaze sensing device to receive said gaze orientation signal, said computer being connected to said response sensing device to receive said response signal, and said computer being programmed to interpret said gaze orientation signal and said response signal to evaluate at least one visual function of the patient.

2. A visual function testing apparatus as recited in claim 1, wherein said scanning device is mountable to the head of a patient.

3. A visual function testing apparatus as recited in claim 1, wherein said computer is programmed to vary at least one characteristic of said flickering image.

4. A visual function testing apparatus as recited in claim 1, further comprising an optical system for directing said flickering image from said scanning system onto the retina of an eye of a patient.

5. A visual function testing apparatus as recited in claim 1, further comprising a redirection element for redirecting said flickering image onto the retina of an eye of a patient.

6. A visual function testing apparatus as recited in claim 5, wherein said redirection element comprises a Fresnel optical element.

7. A visual function testing apparatus as recited in claim 6, wherein said Fresnel optical element comprises a Fresnel mirror.

8. A visual function testing apparatus as recited in claim 6, wherein said Fresnel optical element comprises a Fresnel lens.

9. A visual function testing apparatus as recited in claim 1, further comprising a beam splitter adapted to split said flickering image from said light source to create a separate flickering image for display to each eye of a patient.

10. A visual function testing apparatus as recited in claim 1, wherein said computer is programmed to shift said flickering image to a desired location relative to said gaze orientation of the patient.

11. A method for analyzing at least one visual function of a patient, said method comprising:

providing a light source connected to a computer;

mounting a display device to the head of a patient, said display device including an image scanning system and a gaze sensing device, said display device being connected to said computer;

modulating said light source with said computer to generate a flickering image;

scanning said flickering image from said light source for display to an eye of the patient, with said scanning system;

sensing the orientation of the eye of the patient and generating a gaze orientation signal;

sensing the patient's response to said flickering image and generating a response signal; and interpreting said gaze orientation signal and said response signal with said computer to evaluate at least one visual function of the patient.

12. A method as recited in claim 11, further comprising splitting said flickering image from said light source with a beam splitter, to create a separate flickering image for display to each eye of the patient.

13. A method as recited in claim 11, further comprising shifting said flickering image to a desired location relative to said gaze orientation of the patient.

14. A multiple site visual field testing system, comprising:

a plurality of image display devices, each said display device being constructed and positioned to display a flickering image for at least one eye of the respective patient;

a plurality of response sensing devices, each said response sensing device being adapted to sense a respective patient's response to a visual stimulus and to generate a response signal;

a plurality of local signal processing systems, each said local processing system being connected to a respective said display device to generate said flickering image, each said local processing system being connected to a respective said response sensing device to receive said response signal;

a central processing system connectable to said plurality of local signal processing systems for controlling generation of said flickering images, and for receipt of said response signals from said plurality of local processing systems;

a neural network for automatic interpretation of said response signals; and a central data repository for collection of data from said response signals, and for repetitive training of said neural network.

15. A visual field testing system as recited in claim 14, wherein each said display device is mounted in a substantially motionless relationship to the head of a patient, while allowing the head to move.

16. A visual field testing apparatus as recited in claim 14, wherein said central processing system is connectable to said plurality of local signal processing systems via the Internet.

17. A method for automatically analyzing the visual fields of a plurality of patients, comprising:

providing an image display device, a response sensing device, and a local signal processing device for each of a plurality of patients;

displaying a flickering image for at least one eye of each patient;

sensing each patient's response to said flickering image and generating a response signal for each patient;

controlling generation of each said flickering image and receiving each said response signal with a central processing system; and analyzing at least one characteristic of the visual field of each patient with a central neural network.

18. A method as recited in claim 17, further comprising connecting said central processing system to each said display device, response sensing device, and local signal processing device via the Internet, for controlling the generation of each said flickering image and receiving each said response signal.

* * * * *